US006463121B1

United States Patent
Milnes

(10) Patent No.: US 6,463,121 B1
(45) Date of Patent: Oct. 8, 2002

(54) INTERACTIVE X-RAY POSITION AND EXPOSURE CONTROL USING IMAGE DATA AS REFERENCE INFORMATION

(75) Inventor: Robert Dana Milnes, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/418,167

(22) Filed: Oct. 13, 1999

(51) Int. Cl.[7] ............................................... H05G 1/60
(52) U.S. Cl. ........................... 378/62; 378/98; 378/98.2
(58) Field of Search ..................... 378/62, 98, 98.2; 382/103, 128, 132; 600/424, 425, 427; 128/920, 922

(56) References Cited

U.S. PATENT DOCUMENTS

| | | | | |
|---|---|---|---|---|
| 4,553,254 A | * | 11/1985 | Bach et al. | 378/98 |
| 4,926,452 A | | 5/1990 | Baker et al. | 378/22 |
| 5,054,045 A | * | 10/1991 | Whiting et al. | 378/98.2 |
| 5,111,492 A | * | 5/1992 | Klausz | 378/98.2 |
| 5,117,446 A | * | 5/1992 | Haaker et al. | 378/98.3 |
| 5,123,056 A | * | 6/1992 | Wilson | 382/132 |
| 5,142,557 A | * | 8/1992 | Toker et al. | 378/37 |
| 5,211,165 A | * | 5/1993 | Dumoulin et al. | 600/410 |
| 5,221,283 A | | 6/1993 | Chang | 606/130 |
| 5,253,169 A | * | 10/1993 | Corby, Jr. | 600/431 |
| 5,282,254 A | * | 1/1994 | Chiu et al. | 382/132 |
| 5,289,373 A | * | 2/1994 | Zarge et al. | 600/434 |
| 5,293,574 A | * | 3/1994 | Roehm et al. | 378/98.2 |
| 5,347,570 A | * | 9/1994 | Haaks | 378/98.12 |
| 5,369,678 A | * | 11/1994 | Chiu et al. | 378/62 |
| 5,396,418 A | * | 3/1995 | Heuscher | 378/15 |
| 5,769,640 A | | 6/1998 | Jacobus et al. | 434/262 |
| 5,771,310 A | | 6/1998 | Vannah | 382/154 |
| 5,883,937 A | * | 3/1999 | Schmitt | 378/189 |
| 5,886,353 A | * | 3/1999 | Spivey et al. | 250/370.09 |
| 6,052,476 A | * | 4/2000 | Qian et al. | 382/130 |
| 6,195,450 B1 | * | 2/2001 | Qian et al. | 382/130 |
| 6,215,848 B1 | * | 4/2001 | Linders et al. | 378/98.12 |

* cited by examiner

Primary Examiner—Robert H. Kim
Assistant Examiner—Allen C. Ho
(74) Attorney, Agent, or Firm—Schwegman, Lundberg, Woessner & Kluth, P.A.

(57) ABSTRACT

An X-ray system and method for use in a medical application to supplement or replace fluoroscopy. The X-ray system includes a display device, a gantry having an X-ray generator, a table having an X-ray sensor, and an X-ray control system connected to the display device, the gantry and the table. The X-ray control system includes user input for indicating the position of the next X-ray exposure. The X-ray control system receives X-ray data from the sensor, processes the data to form an X-ray image, displays the X-ray image on the display device and shifts the X-ray generator relative to the X-ray sensor. The amount and direction of shift is accurately determined using data from the previous X-ray image.

24 Claims, 9 Drawing Sheets

INTERACTIVE X-RAY POSITION AND EXPOSURE CONTROL USING IMAGE DATA AS REFERENCE INFORMATION

FIELD OF THE INVENTION

The present invention is related to medical imaging, and more particularly to a system and method for positioning an acquisition device and acquiring an image based on image data.

BACKGROUND INFORMATION

Currently medical X-ray procedures, such as X-ray fluoroscopy, use a high acquisition data rate for X-ray images. The images generated by the X-ray fluoroscopy are then used to manually guide a tool through the internal structure of an opaque body or object (e.g. the human body). Directing this tool, which may be a medical device such as a catheter, through an opaque object is usually quite inefficient and inaccurate since it relies on the operator of the X-ray fluoroscopy device and the X-ray machinery to manually estimate the next position using various types of control techniques developed for this purpose. X-ray fluoroscopy is used for interventional medical procedures such as balloon angioplasty and neuroembolizations. These medical procedures have been extremely successful and widely utilized. Their wide utilization has resulted in X-ray fluoroscopy accounting for over one-half of the diagnostic X-ray dosage. Such wide spread use has, however resulted in documented instances of severe skin injury.

One way to reduce radiation exposure of patients and operators would be to optimize the X-ray image acquisition and filtering techniques used for X-ray fluoroscopy. One such approach uses a combination of lowering the acquisition data rate of the X-ray fluoroscopy and increasing the X-ray image resolution to direct the X-ray fluoroscopy machinery. However, this approach relies on the human operator to manually control the X-ray machinery, which introduces uncertainty.

To-date, there have not been any solutions addressing the uncertainty introduced by an operator manually controlling the X-ray fluoroscopy machinery. Instead, solutions explored in the medical industry have been limited to increasing the efficiency of the X-ray fluoroscopy machinery by increasing the image resolution, or to reducing the radiation exposure for the operator and patient by decreasing the number of noisy images produced by the X-ray fluoroscopy machinery.

What is needed is an X-ray control system, device and method for interactively processing a selection point for an X-ray exposure based on a previous X-ray exposure to improve the productivity and safety of medical X-ray procedures.

SUMMARY OF THE INVENTION

According to one aspect of the present invention, an X-ray system and method is described for use in a medical application to supplement or replace fluoroscopy. The X-ray system includes a display device, a gantry having an X-ray generator, a table having an X-ray sensor, and an X-ray control system connected to the display device, the gantry and the table. The X-ray control system includes user input for indicating the position of the next X-ray exposure. The X-ray control system receives X-ray data from the sensor, processes the data to form an X-ray image, displays the X-ray image on the display device and shifts the X-ray generator relative to the X-ray sensor. The amount and direction of shift is accurately determined using data from the previous X-ray image.

According to another aspect of the present invention, a system and method of positioning an X-ray generator relative to the X-ray sensor is described. X-ray data is received from the sensor and processed to form an X-ray image. The X-ray image is displayed on a display device and a position is selected on the X-ray image. The X-ray generator is shifted relative to the X-ray sensor as a function of the position selected on the X-ray image.

According to yet another aspect of the present invention, a system and method for tracking a first object within a second object is described. X-rays are projected through the second object in the vicinity of the first object, captured and used to generate a display image. The display image is displayed. The appearance of the first object is emphasized within the second object, movement of the first object within the second object is detected and relative position of the second object to the X-ray source is changed as a function of movement of the first object before a new display image is captured.

The X-ray control system, device and method utilizes a computing system to determine the next position of the X-ray fluoroscopy machinery based on the information processed from the previous X-ray image, thus decreasing the uncertainty introduced by a operator manually controlling the X-ray fluoroscopy machinery. The location of the next exposure is also more accurate since it is controlled by an X-ray control system. Such an approach contrasts with current X-ray fluoroscopy techniques that rely upon an operator to guide the X-ray fluoroscopy machinery manually. Accurately directing the X-ray fluoroscopy machinery also reduces the radiation exposure for both operators and the patients.

BRIEF DESCRIPTION OF THE DRAWINGS

In the drawings, where the like number reflects similar function in each of the drawings.

DESCRIPTION OF THE PREFERRED EMBODIMENTS

In the following detailed description of the preferred embodiments, reference is made to the accompanying drawings that form a part hereof, and in which is shown by way of illustration specific embodiments in which the invention may be practiced. It is to be understood that other embodiments may be utilized and structural changes may be made without departing from the scope of the present invention.

Portions of the detailed descriptions that follow are presented in terms of algorithms and symbolic representations of operations on data bits within a computer memory. These algorithmic descriptions and representations are the means used by those skilled in the data processing arts to most effectively convey the substance of their work to others skilled in the art. Each algorithm is a self-consistent sequence of steps leading to a desired result. The steps include those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Figure 1:
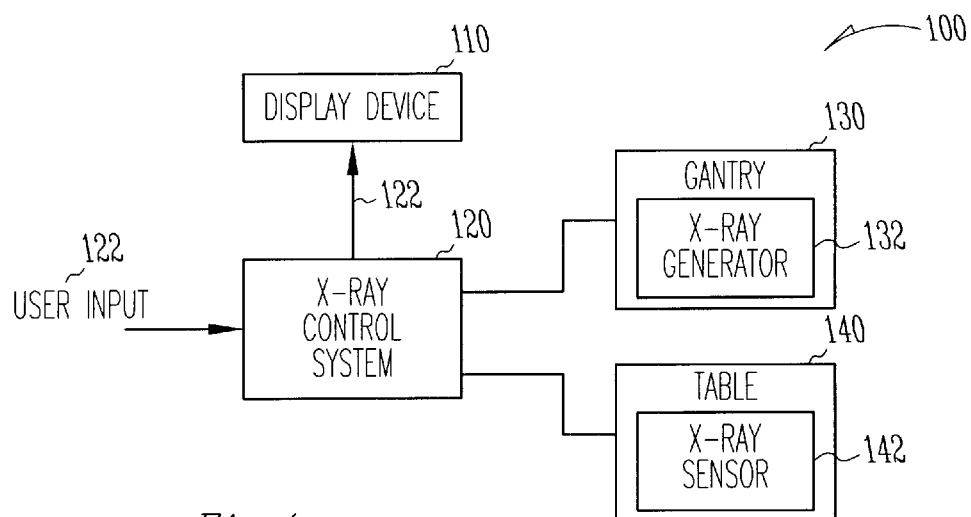
FIG. 1 illustrates one embodiment of an X-ray control system.

An X-ray system 100 is shown in FIG. 1. X-ray system 100 includes a display device 110, an X-ray gantry 130 and a table 140, all connected to an X-ray control system 120. In one embodiment, such as is shown in FIG. 1, X-ray gantry 130 includes an X-ray generator 132; table 140 includes an X-ray sensor 142. In another embodiment, X-ray gantry 130 includes both X-ray generator 132 and X-ray sensor 142 and moves generator 132 and sensor 142 relative to a location on table 140.

X-ray control system 120 stores an X-ray exposure as an image along with the associated positions of X-ray gantry 130 and table 140. The X-ray images are displayed on display device 110 in various configurations. Typically, the last X-ray exposure taken is displayed on the display device 110.

In one embodiment, X-ray control system 120 includes one or more user inputs 122. User inputs 122 direct X-ray control system 120 under operator control of the movement of X-ray gantry 130, or table 140, or both, to a new position between X-ray exposures. In one such embodiment, display device 110 is placed near the operator and he or she uses a pointing device to select the position on display device 110 where he or she desires the next X-ray exposure to be centered. The pointing device may be, but is not limited to, a mouse, a trackball or a touch screen. X-ray control system 120 detects user input 122 and correlates user input 122 to a new X-ray exposure center position or reference point. After a new center position or reference point is determined, X-ray control system 120 moves X-ray gantry 130 and/or table 140 to their required locations for a new X-ray exposure and takes a new X-ray exposure. The new X-ray exposure is then displayed as an image on display device 110.

Figure 2:
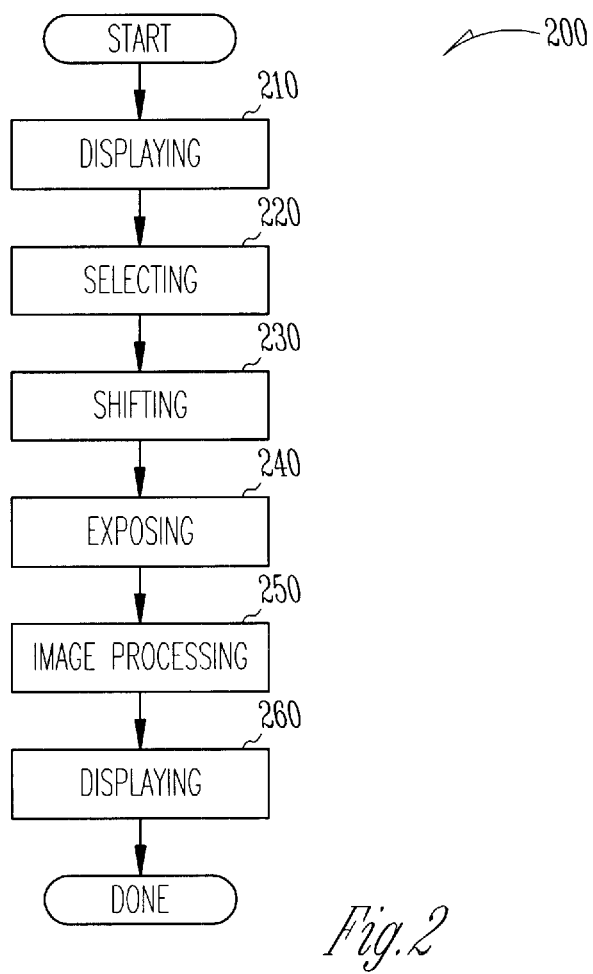
FIG. 2 shown one embodiment of a block diagram for an X-ray control system shown in FIG. 1.

A block diagram shown in FIG. 2 shows one embodiment 200 of the X-ray control method discussed above. At 210, system 100 displays an X-ray image on display device 110.

At 220, an operator selects a position for taking a second X-ray image and at 230, system 100 shifts X-ray gantry 130 or table 140, or both, to the next position. When the shifting is complete, at 240 system 100 requests an X-ray exposure to be taken from gantry 130. At 250, image processing is completed by the control system 120 and, at 260, an image representing the X-ray is displayed on display device 110. This process repeats as often as is necessary to provide the desired X-ray images.

Figure 3:
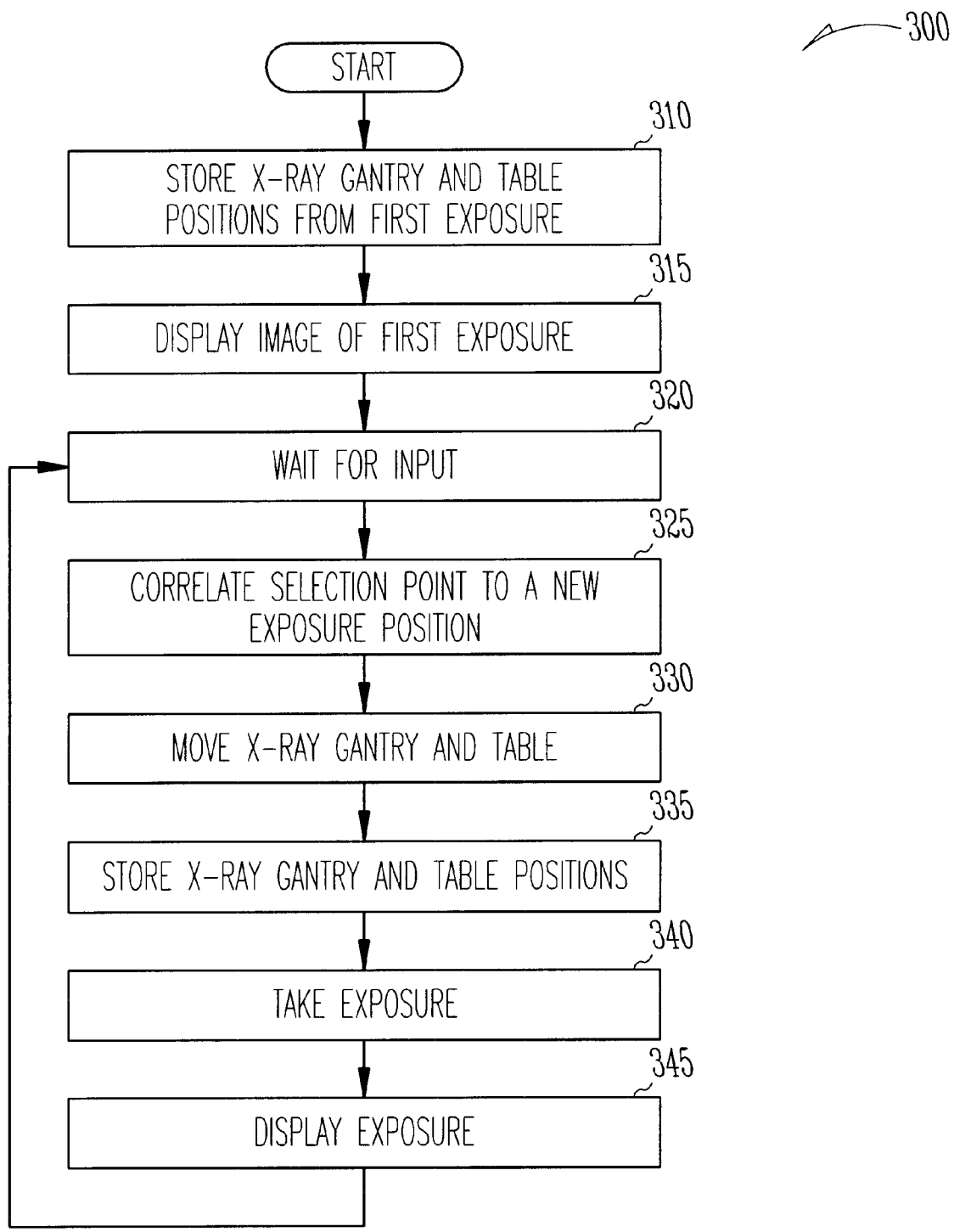
FIG. 3 is one embodiment of a block diagram of an X-ray control system according to FIG. 2.

Another embodiment 300 of the X-ray control method discussed above is shown in FIG. 3. At 310, X-ray gantry and table positions are stored with data from the first exposure. In one such embodiment, X-ray gantry and table positions are stored automatically as part of capturing the first exposure. In another such embodiment, the operator enters X-ray gantry and table positions.

At 315, control moves to 315, where an image representing capture of the first exposure is displayed for the operator. Control then moves to 320, where system 120 waits for input from the operator indicating a location to be used to position gantry 130 and/or table 140 for the next exposure. Once received, control moves to 325, where system 100 correlates the location selected to a new X-ray exposure position. In one embodiment, the location selected on the display is treated as the center position for the next exposure. It should be noted, however, that the location selected does not have to be used as the center position for the next exposure. Instead, the location selected could be interpreted to correlate to other useful reference points for the X-ray fluoroscopy machinery.

At 330, X-ray control system 120 moves the X-ray gantry 130 or table 140, or both, to new positions as a function of the selected location. At 335, control system 120 stores the new position of the gantry 130 and table 140. At 340, a new exposure is taken by X-ray control system 120. At 345, the new exposure is displayed on display device 110. Control then moves to 320, where X-ray control system 120 waits for operator entry of the next selected location.

In one embodiment, X-rays are turned off while system 100 moves to a new location. Since X-rays are not being generated while the X-ray gantry 130 and table 140 are in motion the radiation dosage is effectively reduced. In addition, the position of the X-ray gantry 130 and table 140 is more accurately determined by X-ray control system 120. This is in sharp contrast to traditional methods, which raise health and safety issues related to excess X-ray exposure. Traditional methods, where an operator manually moves the X-ray fluoroscopy machinery, use a high acquisition data rate for X-ray exposures. Because of the high acquisition data rate used with such traditional methods, both operators and patients receive a higher radiation dosage.

Figure 4A:
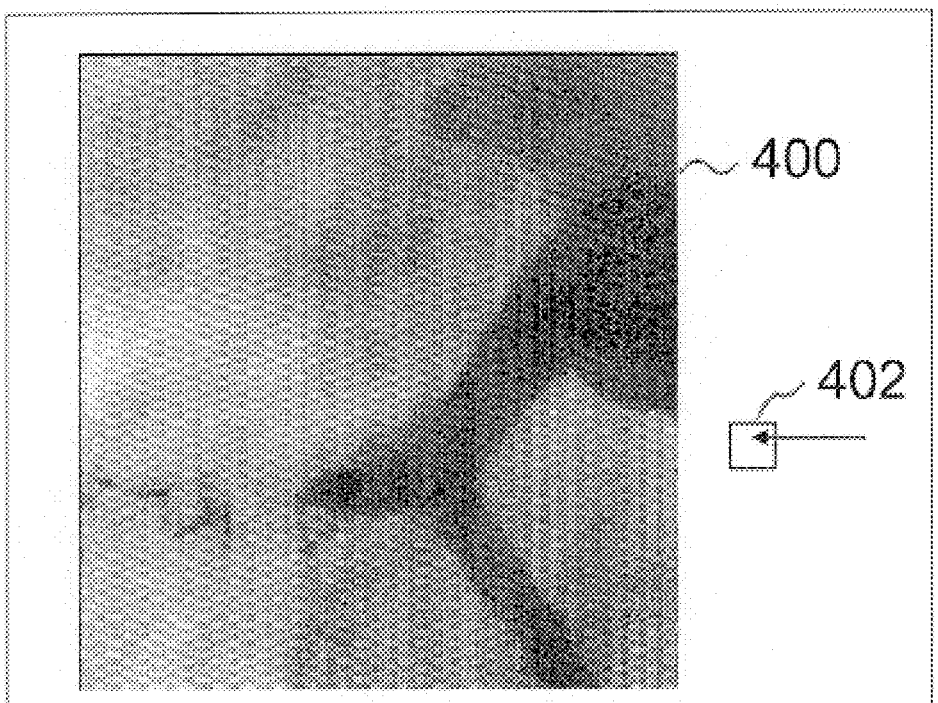
FIGS. 4a and 4b illustrate one embodiment of a selection process for selecting a new X-ray exposure.
Figure 4B:
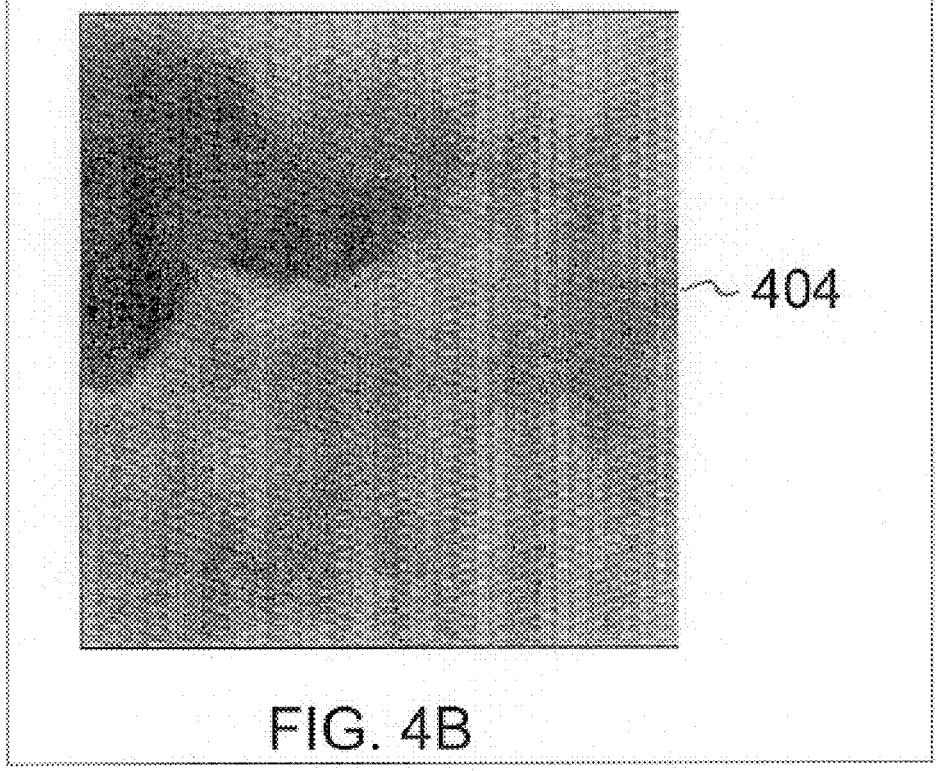
Figures 5A, 5B:
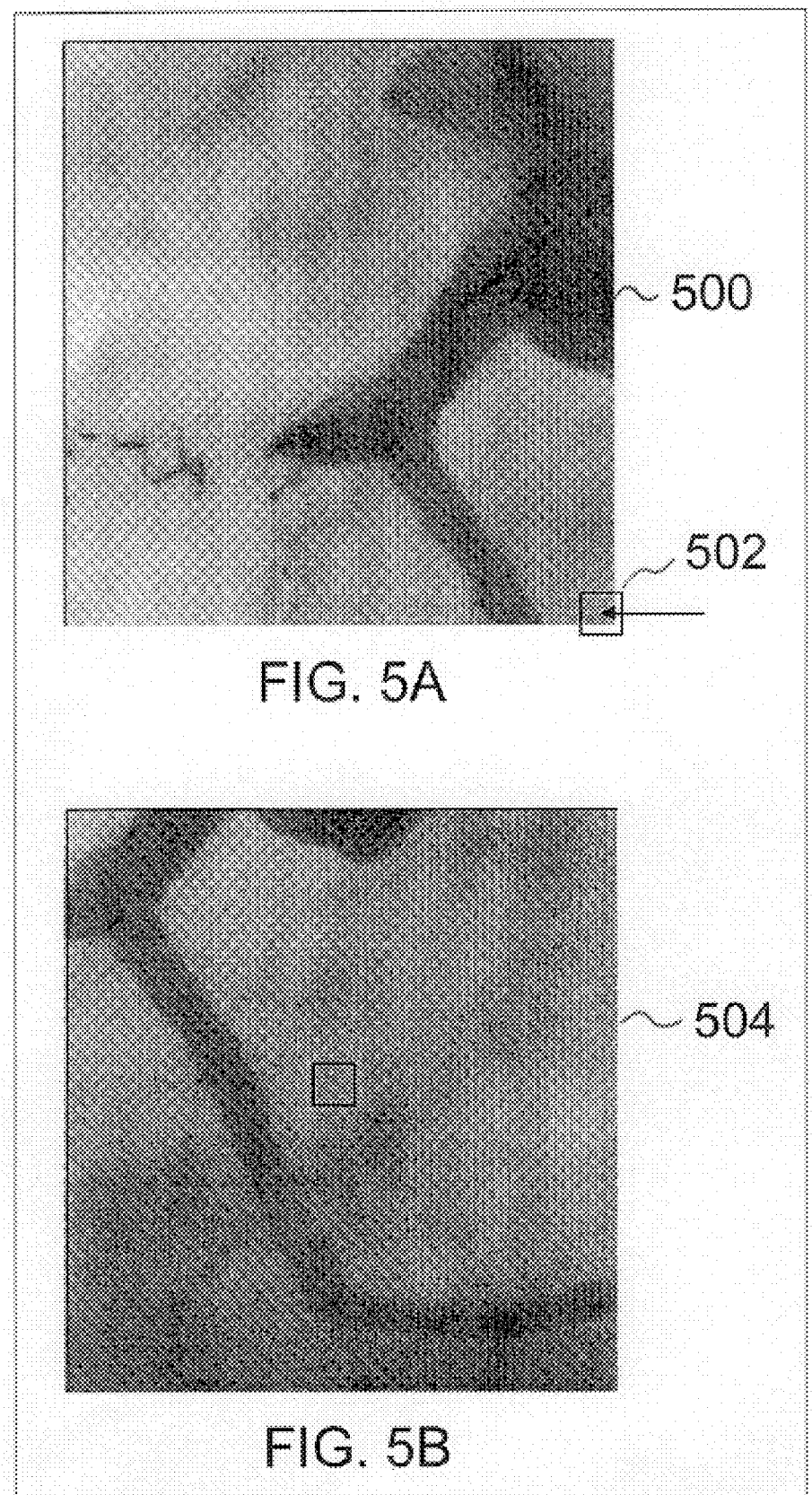
FIGS. 5a and 5b illustrate another embodiment of a selection process for selecting a new X-ray exposure.
Figure 6A:
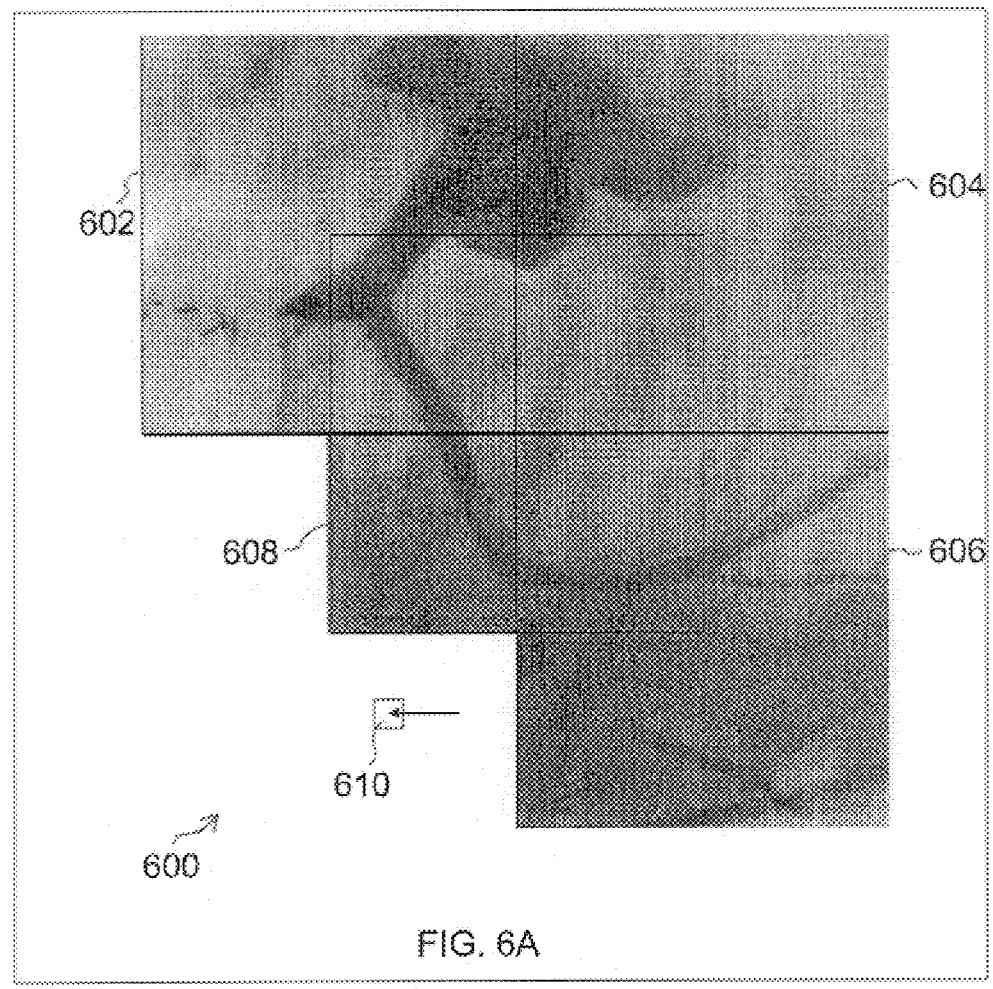
FIGS. 6a, 6b, and 6c illustrate a zoom feature.
Figure 6B:
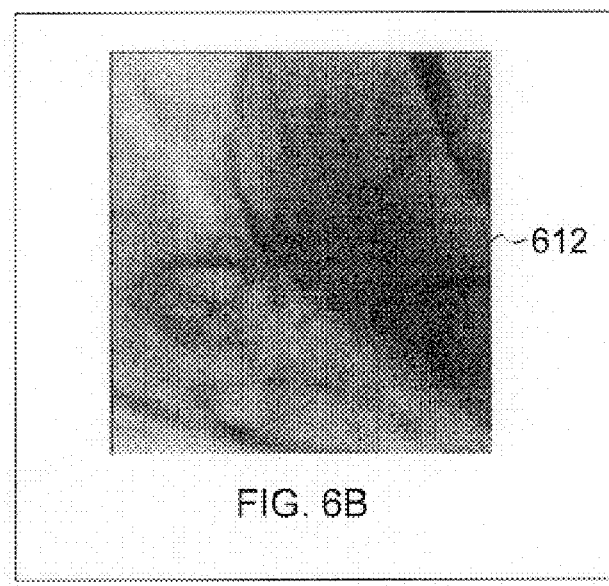
Figure 6C:
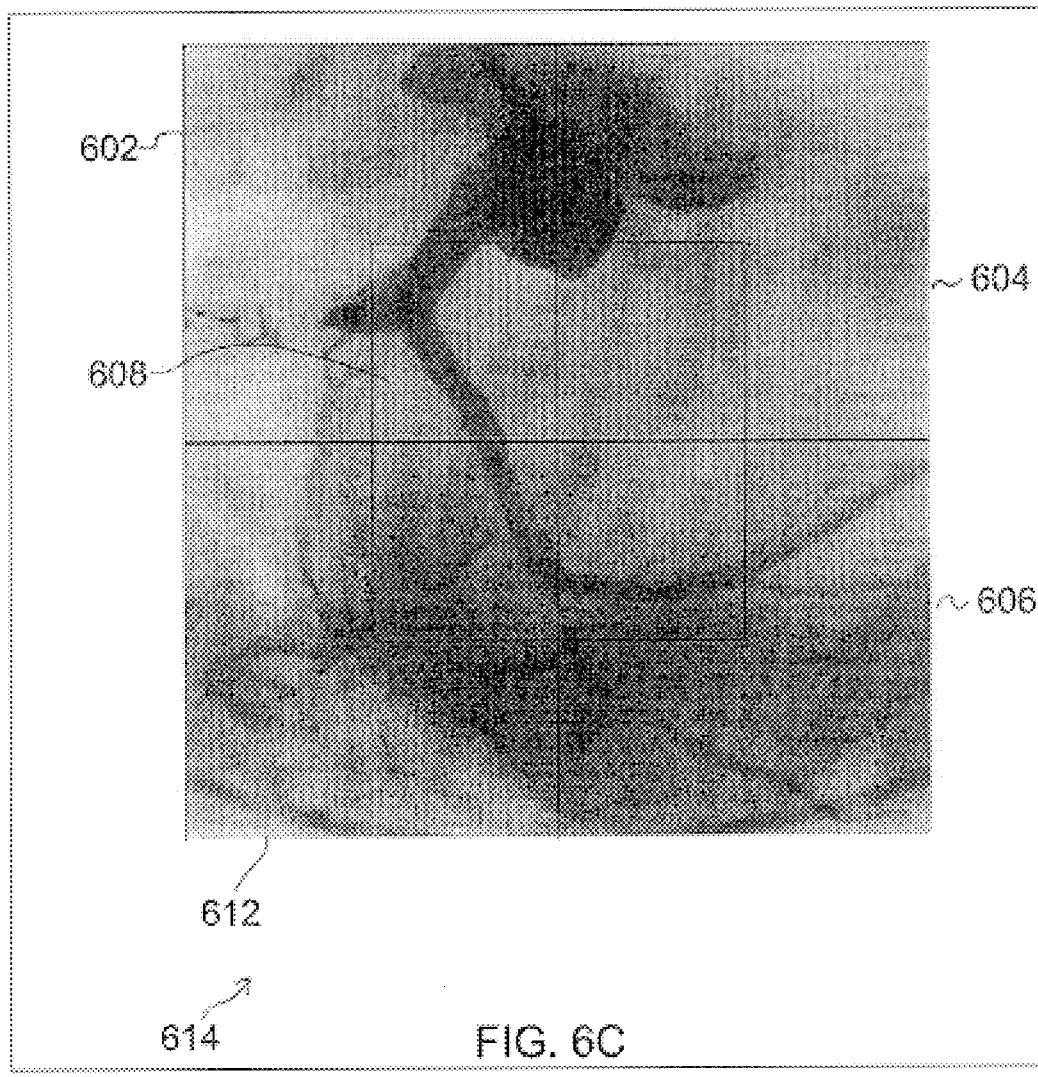

Images representative of successive X-ray image acquisitions are shown in FIGS. 4a and 4b, in FIGS. 5a and 5b and in FIGS. 6a–6c. The example shown in FIGS. 4a and 4b, in FIGS. 5a and 5b and in FIGS. 6a–6c use a rectangular bitmap of a heart taken at the Mayo Clinic using a touch screen display panel. In the embodiment shown in FIGS. 4a–b, a point 402 for a new X-ray exposure is selected by an operator touching outside a first image 400. Control system 120 then processes the selected location to determine a new position for either X-ray gantry 130 or table 140, or both, and an exposure is made. An image representing the resulting exposure is shown as image 404 in FIG. 4b.

In the example shown in FIGS. 5a and 5b, a point 502 within an X-ray image 500 is selected by an operator. Control system 120 then takes a new X-ray exposure, shown as image 504 in FIG. 5b, based on the point selected by the operator.

In one embodiment, X-ray control system 120 includes a zoom feature. Once an operator has processed two or more X-ray exposures, the operator can use the zoom out function to display a image that is a composite of the X-ray images received at that point. One example of such a composite image 600 is shown in FIG. 6a. In the composite image 600 shown in FIG. 6a, images 602, 604, 606 and 608 were taken in some order. The operator displays composite image 600 and uses that image to select the location 610 of the next exposure. If, as is shown in FIG. 6a, a selection is made within the missing quadrant, x-ray gantry 130 and/or table 140 are moved to the appropriate locations. (In one embodiment, however, the location selected must be made in the center of the missing quadrant in order to generate an image covering the entirety of the missing quadrant.)

Once location 610 is selected, an exposure is made and an image such as image 612 shown in FIG. 6b is generated. The operator can use the zoom-out feature to display a new composite image 614 which includes contributions from each of the images 602, 604, 606, 608 and 614. Overlapping areas are merged using standard image processing methods.

In the examples shown in FIGS. 4a–b, 5a–b, and 6a–c, X-ray fluoroscopy is not required while moving the X-ray gantry 130, or table 140, or both, because the spatial distances are determined by X-ray control system 120 based on the point selected by the operator. As a result, X-ray dosage for both operators and patients is greatly reduced.

Figure 7:
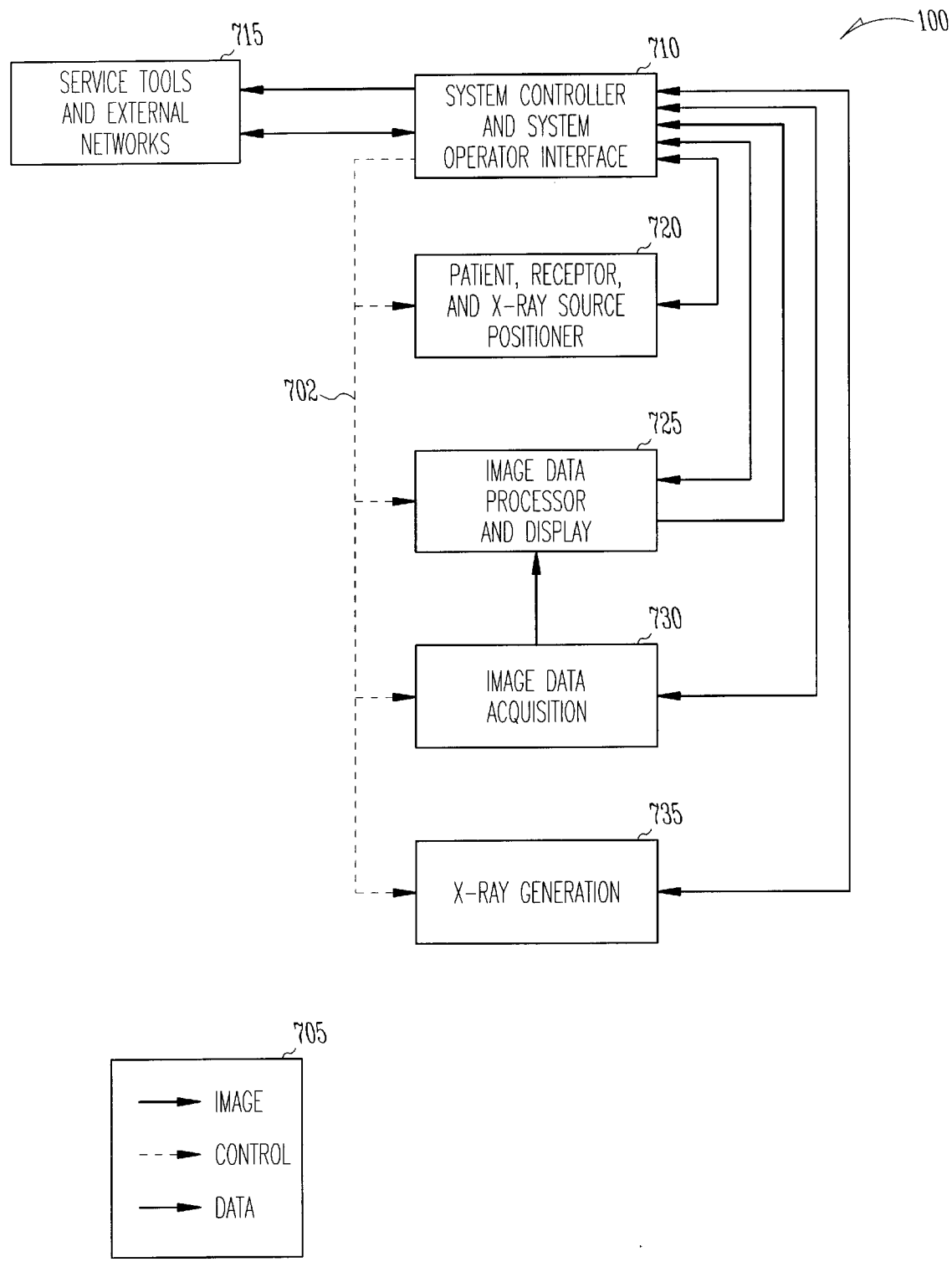
FIG. 7 is an alternate embodiment of the block diagram of FIG. 2.

The block diagram shown in FIG. 7 illustrates another embodiment of X-ray system 100. Each of the blocks for system 100 performs one or more activities as indicated by key 705. In the embodiment shown in FIG. 7, system 100 includes a system controller 710, input/output system 715, a positioner 720, an image processor 725, image acquisition system 730 and X-ray generation system 735. System controller 710 controls each of positioner 720, image processor 725, image acquisition system 730 and X-ray generation system 735 using control lines 702 and data lines 703. Image acquisition system 730 receives X-rays generated by X-ray generation system 735 and forwards data representative of the X-rays received to image processor 725. Image processor 725 includes a display. Image processor 725 generates images 701 based on the data received from image acquisition system 730 and displays the images on its display. An operator selects a location within the image shown on the display and the information regarding the selected location is transferred to system controller 710. System controller 710 processes the information received from the operator and instructs positioner 720 as to the desired positioning of the patient relative to the X-ray source. In one such embodiment, the patient is held stationary while the source and receptor move around the patient. In another embodiment, the table moves relative to a stationary X-ray source. In yet another embodiment, both the table holding the patient and the X-ray source move while positioning for the next exposure.

In the embodiment shown in FIG. 7, input/output system 715 is used to connect to service tools, to external networks or to external monitors. Images 701 captured within system controller 710 can be exported to system 715, where they can be transmitted across a network, read by a service tool or displayed on external display devices.

Figure 8:
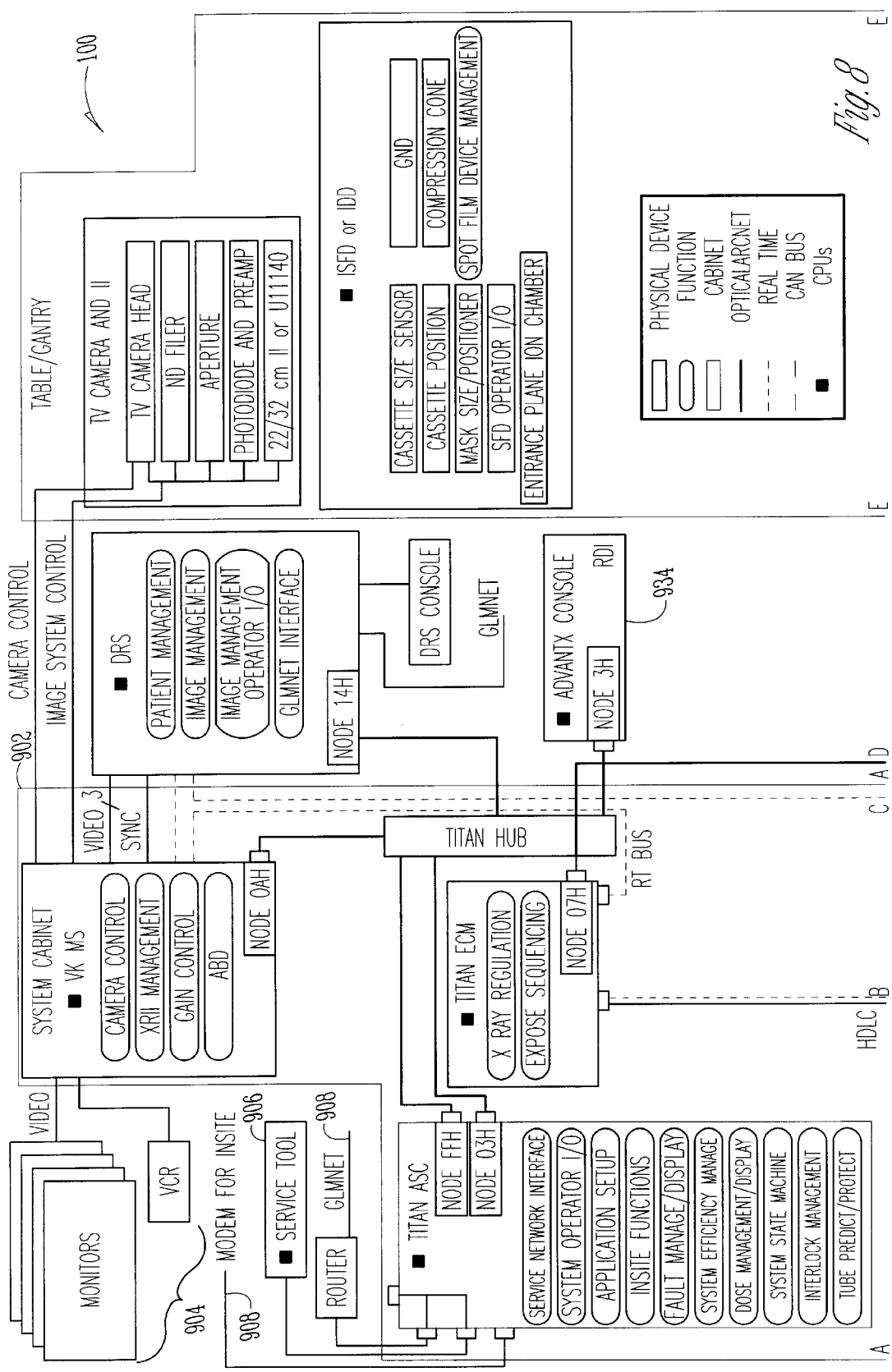
FIG. 8 shows a detailed block diagram of an X-ray system according to the block diagram of FIG. 7.
Figure 8:
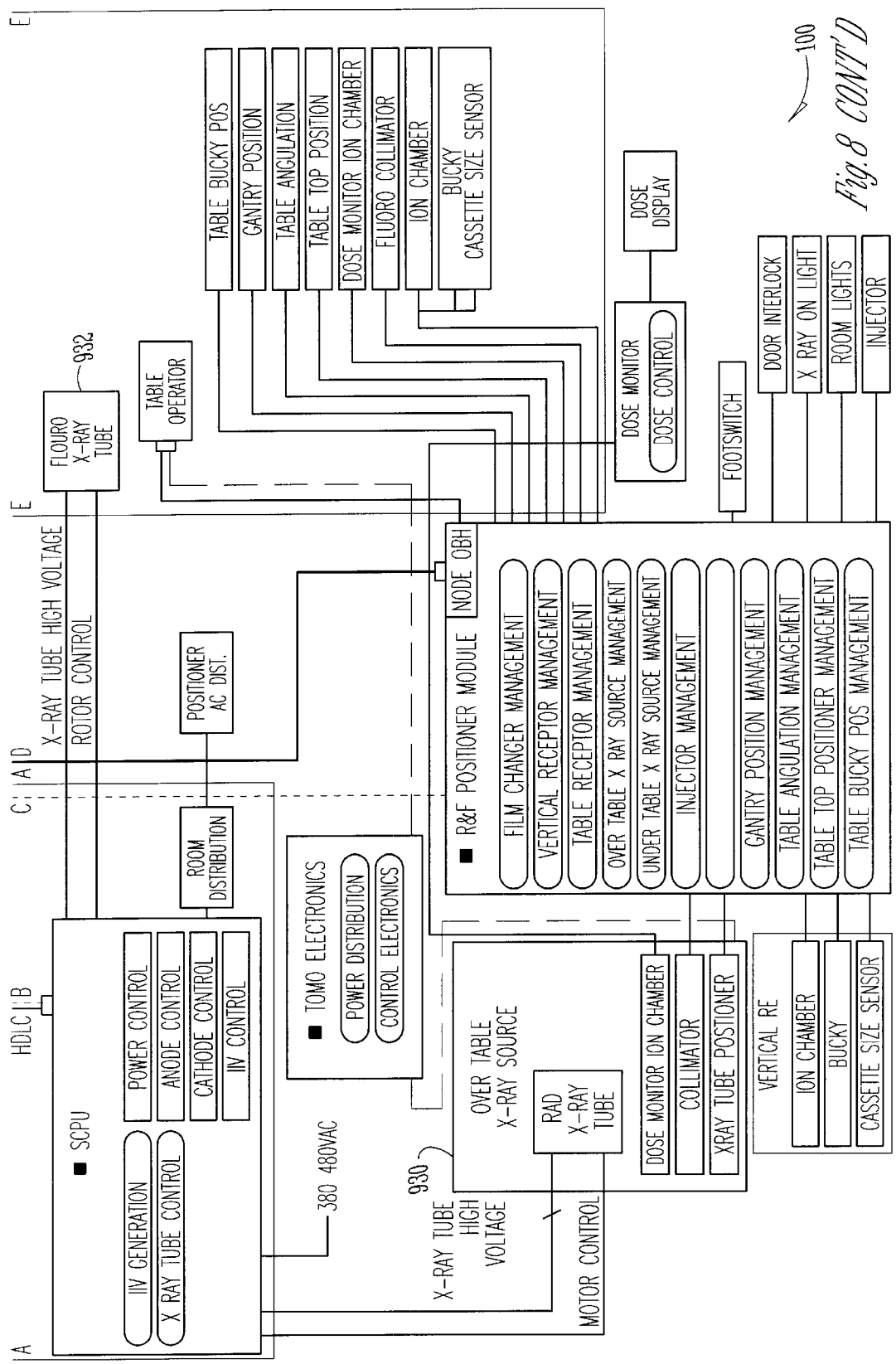

A detailed block diagram of another embodiment of X-ray system 100 is illustrated in FIG. 8. In one embodiment, X-ray system 100 includes system cabinet 902, external video capture and video display devices 904, service tool 906, external network interfaces 908, two X-ray sources 930 and 932, a display 934 and assorted 3data capture and patient positioning controls.

In one embodiment, images are examined in real-time for a change in state or movement of a relevant structure or flow (hereafter referred to as an object.) In one embodiment pattern recognition is used to examine the image for a change in state or movement of a relevant structure or flow. The information obtained from the image itself about the object is correlated to a position in the image and, in one such embodiment, in the patient. When the object changes relative position in the image, the change is tracked automatically by the X-ray control system.

In one such embodiment, control logic is used to track the object and to change the relative position of the patient to the X-ray source to follow the object (for example, moving the table to keep the object centered). In addition, control logic can be used to change the size and dose of the X-ray (e.g., collimating to reduce the size of the image and therefore the dosage to the patient.)

In one such embodiment, display methods are used to highlight the object and to distinguish it from the surrounding anatomy (e.g., using one color to denote a catheter tip and another to represent the vessel wall).

The military and the transportation industry have been creating new technologies related to identifying objects both moving and static in digital images. Such enhancements have even made their way into the mass media where real-time fast moving objects (i.e. a hockey puck) are tracked and enhanced with color so that viewers can follow the object more closely. In the medical industry, Computer Aided Detection has been demonstrated for locating potential breast tumors—although such detection is done off-line rather than in real-time. Since X-ray images are now being created in high-resolution digital format, there is an opportunity to use information contained in the digital image as input to the X-ray control system and allow change in its operational behavior.

Potential benefits of using automatic image data feedback and control as described above include faster procedures, less operator intervention during an X-ray procedure, and less dosage to the operators and patient.

In one embodiment, X-ray control system 120 automatically follows the tip of a catheter while a doctor inserts it into a leg during an embolization procedure. The catheter tip may be centered exactly in the image, or it may be positioned a certain distance from the edge of the image. By using image data feedback, the number, size, and duration of the X-ray images is reduced.

In a second embodiment, X-ray control system 120 automatically follows contrast injected into a body, while it flows through blood vessels in a major artery. In one such embodiment, the size of the image is maintained and, as a result, the radiation dosage to the patient is limited. In one such embodiment, the number and size of the images required is reduced by using information about the bolus location as input to X-ray control system 120.

In a third embodiment, X-ray system 120 enhances anti-collision techniques in X-ray fluoroscopy by recognizing skin, organs, or bones in the X-ray image and using anatomical relationships to avoid collision. Such an approach permits maintaining a smaller distance between patient and the detector, especially during the automatic tracking described above.

In a fourth embodiment, X-ray system 120 changes the color of a catheter tip during insertion so that an operator can locate it more easily.

An advantage of X-ray system 100 is that an operator or control system can interactively select the position of the next X-ray exposure based on image information contained in previous X-ray exposures. In addition, the present X-ray control system more accurately determines the locations of an X-ray, which results in less radiation dosage. In one embodiment, the use of X-ray fluoroscopy is completely eliminated. Furthermore, accurate X-ray exposure locations provide an opportunity to decrease the field of view (FOV), which further reduces X-ray exposure and at the same time increases image quality.

X-ray system 100 therefore provides several overall benefits. There is a reduction in the total radiation dosage to operators and patients when less X-ray fluoroscopy is used. The accurate location of the next X-ray exposure results in faster X-ray medical procedures and also reduces the total radiation dosage to patients and operators. Finally, by using smaller FOV's with X-ray medical procedures, X-ray system 100 increases image quality while decreasing radiation dosage.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. In an X-ray system having an X-ray generator and an X-ray sensor, a method of positioning the X-ray generator relative to the X-ray sensor, comprising:
   displaying a display image, wherein the display image includes data representing an X-ray image;
   selecting a position on the display image; and
   shifting the X-ray generator relative to the X-ray sensor as a function of the position selected on the display image.

2. The method of claim 1, wherein selecting a position on the display image includes pointing at the image with a pointing device.

3. The method of claim 1, wherein selecting a position on the display image includes touching the image.

4. The method of claim 1, wherein selecting a position on the display image includes tracking movement of a first object in the image relative to a second object in the image, wherein the control logic chooses the position selected on the image as a function of movement of the first object relative to the second object.

5. A computer readable medium comprising program code for executing the method of claim 1.

6. An X-ray system, comprising:
   a display device;
   a gantry having an X-ray generator;
   a table having an X-ray sensor; and
   an X-ray control system connected to the display device, the gantry and the table, wherein the X-ray control system receives X-ray data from the sensor, processes the data to form an X-ray image, displays the X-ray image on the display device and shifts the X-ray generator relative to the X-ray sensor as a function of a position selected on the X-ray image.

7. The X-ray system according to claim 6, wherein the display device includes a touch screen and wherein a user indicates the position selected on the X-ray image by touching the image on the touch screen.

8. The X-ray system according to claim 6, wherein the control system includes a pointing device capable of displaying a pointer icon on the display device and wherein a user indicates the position selected on the X-ray image by pointing to the image with the pointing device.

9. The X-ray system according to claim 6, wherein the control system includes control logic for tracking movement of a first object in the X-ray image relative to a second object in the X-ray image, wherein the control logic selects the position selected on the X-ray image as a function of movement of the first object relative to the second object.

10. In an X-ray system having an X-ray generator, an X-ray sensor and a display device, a method of positioning the X-ray generator relative to the X-ray sensor, comprising:
    receiving X-ray data from the sensor;
    processing the X-ray data to form an X-ray image;
    displaying the X-ray image on the display device;
    selecting a position on the X-ray image; and
    shifting the X-ray generator relative to the X-ray sensor as a function of the position selected on the X-ray image.

11. The method of claim 10, wherein selecting a position on the X-ray image includes pointing at the image with a pointing device.

12. The method of claim 10, wherein selecting a position on the X-ray image includes touching the image.

13. The method of claim 10, wherein selecting a position on the X-ray image includes tracking movement of a first object in the image relative to a second object in the image, wherein the control logic selects the position as a function of movement of the first object relative to the second object.

14. A computer readable medium comprising program code for executing the method of claim 10.

15. An X-ray system, comprising:
    a display device;
    a gantry having an X-ray generator;
    a table having an X-ray sensor; and
    an X-ray control system connected to the display device, the gantry and the table, wherein the X-ray control system operates to receive X-ray data from the sensor, process the data to form an X-ray image, display the X-ray image on the display device and, if a user selects a position outside the X-ray image displayed on the display device, shifts the X-ray generator relative to the table as a function of a position selected on the X-ray image.

16. The X-ray system according to claim 15, wherein the display device includes a touch screen and wherein a user indicates the position selected by touching the image on the touch screen.

17. The X-ray system according to claim 15, wherein the control system includes a pointing device capable of displaying a pointer icon on the display device and wherein a user indicates the position selected by pointing to the image with the pointing device.

18. The X-ray system according to claim 15, wherein the control system includes control logic for tracking movement of a first object in the X-ray image relative to a second object in the X-ray image, wherein the control logic selects the position selected as a function of movement of the first object relative to the second object.

19. In an X-ray system having an X-ray generator, an X-ray sensor and a display device, a method of positioning the X-ray generator relative to the X-ray sensor, comprising:
    receiving X-ray data from the sensor;
    processing the X-ray data to form an X-ray image;
    displaying the X-ray image on the display device;
    selecting a position outside the X-ray image; and shifting the X-ray generator relative to the X-ray sensor as a function of the position selected.

20. The method of claim 19, wherein selecting a position includes pointing at the image with a pointing device.

21. The method of claim 19, wherein selecting a position includes touching the image.

22. The method of claim 19, wherein selecting a position includes tracking movement of a first object in the image relative to a second object in the image, wherein the control logic selects the position as a function of movement of the first object relative to the second object.

23. A computer readable medium comprising program code for executing the method of claim 19.

24. In an X-ray system having an X-ray generator and an X-ray sensor, a method of tracking a first object within a second object, comprising:

projecting X-rays through the second object in the vicinity of the first object;

capturing X-rays passing through the second object;

generating a display image as a function of the captured X-rays;

displaying the display image;

emphasizing the first object within the second object;

changing relative position of the second object to the X-ray source as a function of movement of the first object; and capturing a new display image, wherein capturing a new display image includes reducing image size through collimating.

* * * * *

UNITED STATES PATENT AND TRADEMARK OFFICE
CERTIFICATE OF CORRECTION

PATENT NO. : 6,463,121 B1
DATED : October 8, 2002
INVENTOR(S) : Robert D. Milnes It is certified that error appears in the above-identified patent and that said Letters Patent is hereby corrected as shown below:

Column 2,
Line 27, delete "a" before "operator" and insert -- an -- therefor.
Line 43, delete "shown" after "FIG. 2" and insert -- shows -- therefor.

Column 5,
Line 4, delete "a" before "image" and insert -- an -- therefor.

Column 6,
Line 1, delete "3data" in -- data -- therefor.

Signed and Sealed this

Seventeenth Day of June, 2003

JAMES E. ROGAN
*Director of the United States Patent and Trademark Office*